United States Patent
DeLeon et al.

(10) Patent No.: US 7,531,299 B2
(45) Date of Patent: May 12, 2009

(54) IN VITRO UPTAKE OF SPAM 1 (PH-20) BY MAMMALIAN SPERM

(75) Inventors: Patricia A. DeLeon, Bear, DE (US); Hong Chen, Shanghai (CN); Hong Zhang, Newark, DE (US); Genevieve S. Griffiths, Wilmington, DE (US)

(73) Assignee: University of Delaware, Newark, DE (US)

( * ) Notice: Subject to any disclaimer, the term of this patent is extended or adjusted under 35 U.S.C. 154(b) by 134 days.

(21) Appl. No.: 11/007,065

(22) Filed: Dec. 8, 2004

(65) Prior Publication Data

US 2005/0210541 A1 Sep. 22, 2005

Related U.S. Application Data

(60) Provisional application No. 60/528,312, filed on Dec. 9, 2003.

(51) Int. Cl.
*A01N 1/02* (2006.01)

(52) U.S. Cl. .............................. 435/2; 435/375; 530/852

(58) Field of Classification Search ........................ None
See application file for complete search history.

(56) References Cited

U.S. PATENT DOCUMENTS

2005/0210541 A1 9/2005 DeLeon et al.

OTHER PUBLICATIONS

Yeung C-H et al. 1997. Interaction of the human epididymal protein CD52 (HE5) with epididymal spermatozoa from men and cynomolgus monkeys. Mol Reprod Devel 48: 267-275.*
Davis BK. 1982. Uterine fluid proteins bind sperm cholesterol during capacitation in the rabbit. Experientia 38: 1063-1064.*
Mouse Spam 1 (PH-20) Evidence for its Expression in the Epididymis and for a New Category of Spermatongenic-Expressed Genes;Deng et al.;Jl. of Andrology vol. 21 No. 6; 822-832, (2000).
Mouse Epidiymal Spam 1 (PH-20) is Released in Vivo and In Vitro, and Spam 1 is Differently Regulated in Testis and Epididymis; Zhang et al.; Biology of Repro 65, pp. 1586-1593, (2001).
Mouse Edididymal Spam 1 (PH-20) is Released in the Luminal Fluid with its Lipid Anchor; Zhang et al.; Journal of Andrology, vol. 24. No. 1—Jan./Feb. 2003; pp. 51-58.
Spam 1 (PH-20) Protein and mRNA expression in the epididymides of humans and macaques: utilizing laser microdissection/RT-PCR; Evans et al.; Repro Bio and Endo; pp. 1-12; 2003.
Mouse Spam 1 (PH-20) is a Multifunctional Protein: Evidence for its Expression in the Female Reproductive Tract; Zhang et al.; Biology of Reproduction 69, 446-454, (2003).
Spam 1 (PH-20) Expression in the Extratesticular Duct and Accessory Organs of the Mouse: A Possible Role in Sperm Fluid Reabsorption; Zhang et al.; Biol of Repro 71 1101-1107, (2004).
Lin, Ying et al. "A Hyaluronidase Activity of the Sperm Plasma Membrane Protein PH-20 Enables Sperm to Penetrate the Cumulus Cell Layer Surrounding the Egg"; The Journal of Cell Biology, vol. 125, No. 5, Jun. 1994; pp. 1157-1163.
Seaton, Gavin, J. et al.; "Rat Sperm 2B1 Glycoprotein (PH-20) Contains a C-Terminal Sequence Motif for Attachment of a Glycosyl Phosphatidylinositol Anchor Effects"; Biology of Reporduction 62, pp. 1667-1676 (2000).
Myles, Diana G., et al.; "Why Did the Sperm Cross the Cumulus? To Get to the Oocyte. Functions of the Sperm Surface Proteins PH-20 and Fertilin in Arriving at, and Fusing with, the Egg"; Biology of Reproduction 56, pp. 320-327 (1997).
Martin-DeLeon, Patricia A. "epididymal SPAM 1 and its impact on sperm function"; Molecular and Cellular Endocrinology 250 (2006); pp. 114-121.

* cited by examiner

*Primary Examiner*—Lora E Barnhart
(74) *Attorney, Agent, or Firm*—McCarter & English (57) ABSTRACT

The invention relates to the in vitro transfer of the Sperm Adhesion Molecule 1 (SPAM 1) to spermatozoa. The SPAM1 protein can be obtained from the epididmys or the uterus and should have an intact lipid anchor. The SPAM 1 protein attaches to the surface of mammalian spermatozoa via it's lipid anchor in an in vitro environment in order to increase the sperm's capability of fertilizing an egg.

12 Claims, 5 Drawing Sheets

IN VITRO UPTAKE OF SPAM 1 (PH-20) BY MAMMALIAN SPERM

CROSS REFERENCE TO RELATED APPLICATIONS

This application claims the benefit of U.S. Provisional Application No. 60/528,312, filed Dec. 9, 2003, the contents of which are incorporated herein by reference.

FEDERALLY SPONSORED RESEARCH

The work described in this application was sponsored by the National Institute of Health Under Contract Number R01HD38273.

FIELD OF THE INVENTION

This invention relates to the transfer of the Sperm Adhesion Molecule 1 (SPAM 1) to spermatozoa. Specifically, the invention relates to the attachment of SPAM 1 to the surface of mammalian spermatozoa via it's lipid anchor in an in vitro environment in order to increase the sperm's capability of fertilizing an egg.

BACKGROUND OF THE INVENTION

Many couples throughout the world have the unfortunate problem of being unable to produce progeny, or, in other words, are infertile. Interestingly, of those infertile couples, approximately 50% are affected because of a problem with the male. A technique that has been found to be somewhat effective with some such couples is in vitro fertilization (IVF), also referred to as human assisted reproductive technology (ART). Although ART has made great strides during the past decade, it is still a relatively inefficient technology. The mean clinical pregnancy rate (CPR) in the U.S. was 35% according to data for 1998 (SART Report, 2000).

During their transit through the epididymis, spermatozoa undergo biochemical and morphological changes to acquire motility and the ability to fertilize an oocyte in vivo. Much of the biochemical changes that occur during this maturation process involve plasma membrane molecules. These changes are believed to be of critical importance because the sperm surface is involved in intercellular and intracellular aspects of fertilization.

A functional marker of sperm fertilizing capacity and for success of in vitro fertilization is sperm hyaluronidase. Sperm hyaluronidase is now known to be the sperm membrane protein called the Sperm Adhesion Molecule 1 (SPAM 1 or PH-20). The molecule is the most widely conserved mammalian sperm membrane protein and is known to play at least three major roles in fertilization.

Via its neutral insoluble hyaluronidase activity, SPAM1 is primarily responsible for the dispersion of the cumulus matrix which forms the first formidable barrier surrounding the oocyte. The molecule also has a hyaluronic acid (HA) receptor which plays a role in the intracellular signaling that is responsible for the acrosome reaction. This reaction releases from the sperm soluble hyaluronidase with an acidic catalytic activity which plays a role in penetrating the zona pellucida and the dispersion of hyaluronic acid in the perivitelline space, the other barriers surrounding the egg. Finally, the adhesion domain found in the C-terminus of the molecule is responsible for the secondary binding of the sperm to the zona pellucida, after the acrosome reaction has occurred. This secondary binding, along with the acidic hyaluronidase activity, is necessary to assist the sperm in navigating the zona pellucida.

Unlike somatic ubiquitous hyaluronidases that are active only at acidic pH, SPAM 1 has hyaluronidase activity at both neutral and acidic pHs, which arise from two different regions within the hyaluronidase domain. The neutral enzyme activity, which is predominantly in the insoluble membrane-bound SPAM 1, is necessary for sperm to penetrate the (HA)-rich extracellular matrix of the cumulus cells surrounding the oocyte. The acidic enzyme activity is present in soluble SPAM 1 that is generated during the acrosome reaction (AR), after cleavage at its carboxy terminus. In primate sperm where membrane-bound SPAM 1 is a 64-kDa protein, the proteolytically cleaved secretory form that is released after the AR is 53 kDa.

Originally, SPAM 1 was thought to be testis-specific. However, it has now been documented that SPAM 1 is also expressed in all three regions of the epididymis (i.e. caput, corpus and cauda) as well as the uterine epithelium during estrus/menstrual cycle. This indicates that it is involved in both sperm maturation and storage in the male and also the final sperm maturation that occurs in the female (capacitation).

To date, SPAM 1 has been found to be expressed in the epididymis of at least four mammalian species (mice, rats, macaques, and humans). This conservation of the expression of SPAM1 in the epididymis suggests that it plays an important functional role in mammalian sperm maturation, the primary function of the epididymis. Epididymal SPAM1 has been characterized in the mouse where it has been shown to be released in vitro as well as in vivo, demonstrating that it is a secretory protein. Importantly, SPAM1 is secreted in the epididymal luminal fluid in both a soluble and a membrane-bound vesicular form; the latter has been shown to possess its lipid glycosyl phosphatidyl inositol (GPI) anchor in an intact form. An intact GPI anchor on epididymal SPAM1 allows the protein to bind to the sperm plasma membrane during their transit in the epididymis to enhance the level of pre-existing molecules obtained from the testes, and thus increase the fertilizing competence of sperm.

Because the SPAM 1 gene is widely conserved among mammals and because its dual pattern of expression in the male (i.e. in the testis and epididymis) is conserved in at least the four species mentioned above, it is likely that the secretion of epididymal SPAM1 is also conserved. This is further supported by evidence that SPAM1 is conserved among mammals in the female uterine epithelium where it is expressed as a secretory protein as well. Accordingly, human SPAM 1 is expected to be secreted in the epididymis, where it has an important, putative role in sperm maturation.

Further, it is believed that SPAM1 is produced independently in the testis and epididymis thus revealing that testicular SPAM1 and epididymal SPAM1 are different glycoforms and that the latter shares identical glycans with caudal sperm. As such, it seems likely that epididymal SPAM1 is a unique isoform, not a redundant protein, further supporting the position that it plays a specific role in sperm maturation in humans where SPAM1 is the only reproductive hyaluronidase in the cluster on chromosome 7q31.

Recently, a soluble recombinant human SPAM1/PH-20 hyaluronidase (rHPH-20) was expressed and purified with high enzyme activity (approximately 75,000 Units/mg) from a stable transfected CHO cell line developed in a chemically defined, protein-free, tissue culture system (Kennedy C., Kunda A., Bleil J. D., Frost G. I., Bookbinder L. H. *Dispersion of the cumulus matrix with a highly purified recombinant* human hyaluronidase (*RHUPH*20), Hyaluronan 2003, Oct. 11-16, Poster #133, The Cleveland Clinic and Matrix biology Institute). While this product has superior enzymatic activity compared to slaughter-house-derived hyaluronidase preparations, it has not been engineered to assist the sperm protein in performing its receptor activity, necessary for intracellular signaling, or its adhesion activity and the ensuing acidic enzymatic penetration of the zona pellucida. In addition, it is important to also note that the lipid anchor was removed from that preparation of the protein, thus eliminating the ability of the molecule to chemically attach to the sperm membrane and thus function in other important aspects other than its enzymatic hyaluronidase activity.

There is therefore a need for an in vitro process for presenting SPAM1 to sperm such that it binds at its in situ location on sperm thus increasing the sperms' capability of performing the additional steps required for fertilization.

SUMMARY OF THE INVENTION

In accordance with this invention, there is provided a method for attaching at least one Sperm Adhesion Molecule 1 protein to one or more sperm in an in vitro environment, the method comprising, in an in vitro environment, exposing said one or more sperm to said at least one Sperm Adhesion Molecule 1.

The invention is further directed to a composition comprising one or more sperm comprising at least one in vitro-bound Sperm Adhesion Molecule 1.

The invention is additionally directed to a method for fertilizing a mammalian egg comprising the following steps:
A. attaching at least one Sperm Adhesion Molecule 1 protein to a sperm in an in vitro environment; and
B. co-incubating the sperm of step A with the mammalian egg under conditions necessary for in vitro fertilization.

The invention is finally directed to a method for fertilizing a mammalian egg comprising the following steps:
A. attaching at least one Sperm Adhesion Molecule 1 protein to a sperm in an in vitro environment; and
B. introduce the sperm of step A to the mammalian egg in vivo under conditions necessary for artificial insemination.

DETAILED DESCRIPTION OF THE INVENTION

It should be noted at the outset that the Sperm Adhesion Molecule 1 will be referred to throughout this document as either SPAM 1 or Spam 1. The differences are used to distinguish the source of the protein. Specifically, "SPAM 1" refers to the protein in general, including that generated in humans, whereas "Spam 1" will only refer to that protein obtained from mouse. It should be further noted, however, that as described earlier, the expression of SPAM1 in the extratesticular pathway, primarily the epididymis, has been identified in four mammalian species (humans, macaques, rats and mice). This conservation of the expression of SPAM1 in the epididymis indicates that it plays an important functional role in sperm maturation, the primary role of the epididymis. The characterization of epididymal Spam1 in the mouse, where it is secreted in vitro as well as in vivo, demonstrates that it is a secretory protein. Thus human SPAM1, and for that matter, all mammalian SPAM1, is expected to be found in the epididymal and uterine luminal fluids.

SPAM1 is secreted in the luminal fluids in both a soluble and an insoluble, membrane-bound form, which is the more predominant form. Importantly, the insoluble, membrane-bound form possesses its lipid GPI anchor in an intact form. With an intact GPI anchor the molecule can bind to the sperm membrane to enhance the level of pre-existing molecules obtained from the testes. Therefore, it is preferred that the acquisition of SPAM 1 on the sperm be done in an insoluble form as it is the most effective.

It is thus an important finding of this invention that a productive method for enhancing the ability of the sperm in performing its neutral enzymatic activity for dissolution of the cumulus cells, its receptor activity necessary for intracellular signaling as well as assisting the sperm in its adhesion activity and the ensuing acidic enzymatic penetration of the zona pellucida, is by the acquisition of the insoluble form of SPAM 1 by the sperm. In particular, it is a finding of this invention that sperm can bind epididymal SPAM1 when exposed in vitro to appropriate quantities of luminal fluid and that this acquisition significantly increases the sperms' potential to penetrate the cumulus cells and produce fertilized ova.

An advantage of the present invention is that the acquisition of SPAM1 on sperm enhances the ability of sperm to function beyond the neutral enzymatic (hyaluronidase) activity and to be able to increase intracellular signaling and adhesion activities of the molecule, either in vivo or in vitro.

In particular, this invention has tremendous application for increasing the success of in vitro fertilization for which a functional marker for sperm fertilizing capacity is hyaluronidase. As such, males who produce sperm and are infertile or subfertile, such as, for example, those having rearrangements involving chromosome 7Q32-QTER (location of the SPAM1 gene), may be able to increase their chances of producing children by increasing the amount of the SPAM 1 protein on the sperm surface. It is thus anticipated that this invention will lead to increased rates of in vitro fertilizing sperm which will benefit human in vitro fertilization. It also is anticipated that it would lead to increased in vivo fertilization after artificial insemination. These and other related techniques would be applicable not only to humans, but also domestic and production animals, and potentially many other related uses as well.

Sources of SPAM1 Protein

It is contemplated that any source of insoluble SPAM1 having an intact lipid anchor can be used for purposes of this invention. One viable preferred source is epididymal fluid containing SPAM1. SPAM1 is known to be secreted in vivo in vesicles in the epididymal epithelium and in vitro in the medium of cultured cells in both a soluble and a membrane-bound form, the latter being in the form of epididymosomes which contain the lipid anchor. An alternative viable source is uterine luminal fluid containing SPAM1. In both cases, it is preferred that the luiminal fluid be sperm-free.

Some alternative sources include SPAM1 (containing the lipid anchor) isolated and purified from either the epididymal or uterine fluid, and potentially even he testes, using known methods in the art. Further, SPAM1 (containing the lipid anchor) can be prepared or obtained using recombinant techniques known in the art. Finally, sperm hyaluronidase in the form of bovine hyaluronidase preparations can be obtained commercially.

In Vitro Binding of SPAM1 to Sperm

In a preferred process for producing sperm having in vitro-bound SPAM1, sperm is exposed to SPAM1-containing dilute epididymal luminal fluid, preferably containing SPAM1 protein concentrations in range of 0.1-2.0 mg/ml of total protein and more preferably 0.5-1.5 mg/ml of total protein. Binding of the protein to the sperm occurs immediately upon contact. However, it is preferred that the sperm be exposed to or incubated with the luminal fluid for a period ranging from 5-120 minutes, and more preferably 30-50 minutes in order to allow for appropriate transfer of SPAM1 to the sperm. Transfer of SPAM1 to the surface of the sperm is vesicle-mediated in the same manner as occurs naturally in the epididymosome-spermatozoa interactions in vivo during epididymal sperm maturation.

While protein concentrations may vary in the ranges set froth above, it is notable that an excess of the binding of SPAM 1 protein in the sperm may cause the sperm to prematurely acrosome react before reaching the zona pellucida (the inner barrier of the oocyte). Thus, optimal levels of SPAM 1 will vary between species and even individuals. Therefore, titration of optimal levels of the protein may be necessary to regulate the amount of SPAM1 used in the co-incubation for different species.

The details of a preferred embodiment of the method of the invention relating to the in vitro binding of SPAM1 to sperm will be described herein with specific reference to mouse Spam 1, but is not intended to be a limiting embodiment of the invention. As described throughout this document, epididymal SPAM1 is believed to be expressed in the epididymis of all mammalian species and, therefore, the method of the invention applies to all mammals. Those having ordinary skill in the art are familiar with the techniques described herein and can determine the appropriate modifications necessary to adapt this process to other mammalian species.

In a preferred process for testing this method of the invention, it is preferred that murine epididymal Spam 1 secreted in the lumen be acquired by mouse sperm, either from the diluted fluid or from epididymosomes isolated from the fluid. One example would be to use sperm from Spam 1 knockout (K/O) mice and luminal fluid from the Rb(6.16)/Rb(6.15) sperm-free mutant mice. The luminal fluid from the latter is free of sperm contaminants and the K/O sperm are free of SPAM 1. Sperm and luminal fluid are collected by standard methods well known in the art. The sperm and luminal fluid are then co-incubated in optimal conditions thus providing an opportunity for transfer of the Spam 1 to the sperm. Following incubation, sperm are washed to remove physically adhering molecules, and then processed for immunochemical detection of Spam 1. The resulting sperm contain Spam 1 that is chemically bound to the membrane via the lipid anchor.

Sperm in which SPAM 1 content is enhanced after in vitro uptake will have increased levels of fertilization rates. As discussed above, the rate of acrosome reaction is dependent on the level of SPAM 1 on the membrane. For example, in Rb(6.16) homozygote mice which have only 43% the normal Spam 1 level, the level of HA-induced acrosome-reacted sperm was found to be significantly lower than that of wild-type mice (see Example 1).

The preferred optimization of conditions for sperm binding of SPAM1 and in vitro uptake include i) pH ranging from about 5.7 to about 7.5, and more preferably, pH of 7.4; ii) temperature ranges from about 32° C. to about 37° C.; and iii) Zinc ($Zn^{+2}$) levels preferably in a range from about 0.1 to 1.5 mM. Zinc is found in high concentrations in the epididymis and is therefore a physiologically relevant condition for the in vitro transfer of epididymal proteins to sperm. As for a preferred source of epididymal luminal fluid, wild-type sperm from ICR (well known strains developed by the Institute for Cancer Research) or any outbred mice is the most preferred, although other sources such as sperm-free mutant mice could be used in this invention. In the case of wild-type luminal fluid, it should first be subjected to centrifugation to remove sperm, and complete removal can be confirmed by microscopic examination of the fluid.

Improved Oocyte Fertilization with Sperm Having In Vitro-Bound SPAM1

To determine the impact of in vitro binding of epididymal SPAM1 to sperm on fertilizing ability, sperm obtained after exposure to SPAM1 are exposed to unfertilized mammalian eggs. In the examples herein, sperm obtained after exposure to luminal fluid during capacitation in vitro were used to inseminate cumulus-intact oocytes (eggs) from females in in vitro fertilization assays. Example 3 sets forth a specific assay wherein Spam1-bound sperm was used to inseminate freshly released cumulus-intact eggs from superovulated ICR females in a known in vitro fertilization assay. Eggs were monitored during incubation for up to 7 hours to detect the progress of cumulus cell-removal and fertilization, and significant increases were noted for sperm incubated in the presence of Spam 1-containing luminal fluid. While the in vitro assay set forth in example 3 is a preferred assay for determining the capabilities of the invention, application of this invention to any mammal can be accomplished using any known in vitro fertilization techniques. In vitro fertilization techniques are well-known in the art and the method of the invention does not involve processes that will effect or alter the procedures associated with these general in vitro fertilization techniques.

As described earlier, the sperm having in vitro-bound SPAM1 can also be used in in vivo fertilization using known artificial insemination techniques. In particular, the sperm having in vitro-bound SPAM1 are introduced to the mammalian egg in vivo under conditions necessary for artificial insemination. The compositions and methods of this invention will not affect artificial insemination procedures, which are well known in the art.

Having now-generally described the invention, the same will be further described by reference to certain specific examples which are provided herein for purposes of illustration only and are not intended to be limiting unless otherwise specified.

EXAMPLES

Example 1

Transfer of SPAM 1 to the Surface of Mammalian Sperm In Vitro

Introduction and Rationale

The challenge in detecting sperm binding of epididymal Spam1 (ES) is distinguishing ES from testicular Spam1 (TS) on sperm. To circumvent this problem we have taken advantage of Spam1 knockout (K/O) mice. The sperm from these mice do not express the protein on their surface as would occur with normal, wild-type mice. Specifically, such mice are genetically altered such that the Spam 1 gene is ablated and, therefore, its function is eliminated. These sperm make it possible to observe ES binding in vitro without the confounding presence of TS. Epididymal luminal fluid free of sperm contaminants is used with K/O sperm which are free of Spam1. Thus Spam1 found on the sperm after washing to remove physically adhering molecules, and processing for immunochemical detection, are molecules that are chemically bound to the membrane via the lipid anchor.

Spam1-deficiency of Spam1 K/O mice was confirmed by PCR genotyping, performing Northern analysis on testicular RNA, and by immunocytochemistry (ICC) on sperm. Spam 1 is transferred to the surface of these sperm in vitro at 37° C. after co-incubation and exposure to epididymal luminal fluid or epididymosomes. Epididymosomes are insoluble membrane-bound particles obtained after ultracentrifugation of the epididymal fluid and thus have a more concentrated form of the protein.

The luminal fluid was obtained from Rb(6.16)/Rb(6.15) double heterozygous mutant mice that are known to produce Spam 1 in their epididymides and which are devoid of sperm due to spermatogenic arrest resulting from the translocation chromosomes. The murine epididymal epithelium releases Spam 1 both in vivo and in vitro. Importantly, the Spam1 is released with its lipid anchor intact.

In the case of the sperm-free mice the luminal fluid was released from the epididymides of the sperm-free mice by mincing them in M2 medium. The sperm from the Spam 1 K/O mice were then placed in a dish with the released luminal fluid for co-incubation. Co-incubation was for 2 hours at 37° C. in a pH of approximately 6.5.

Figure 2:
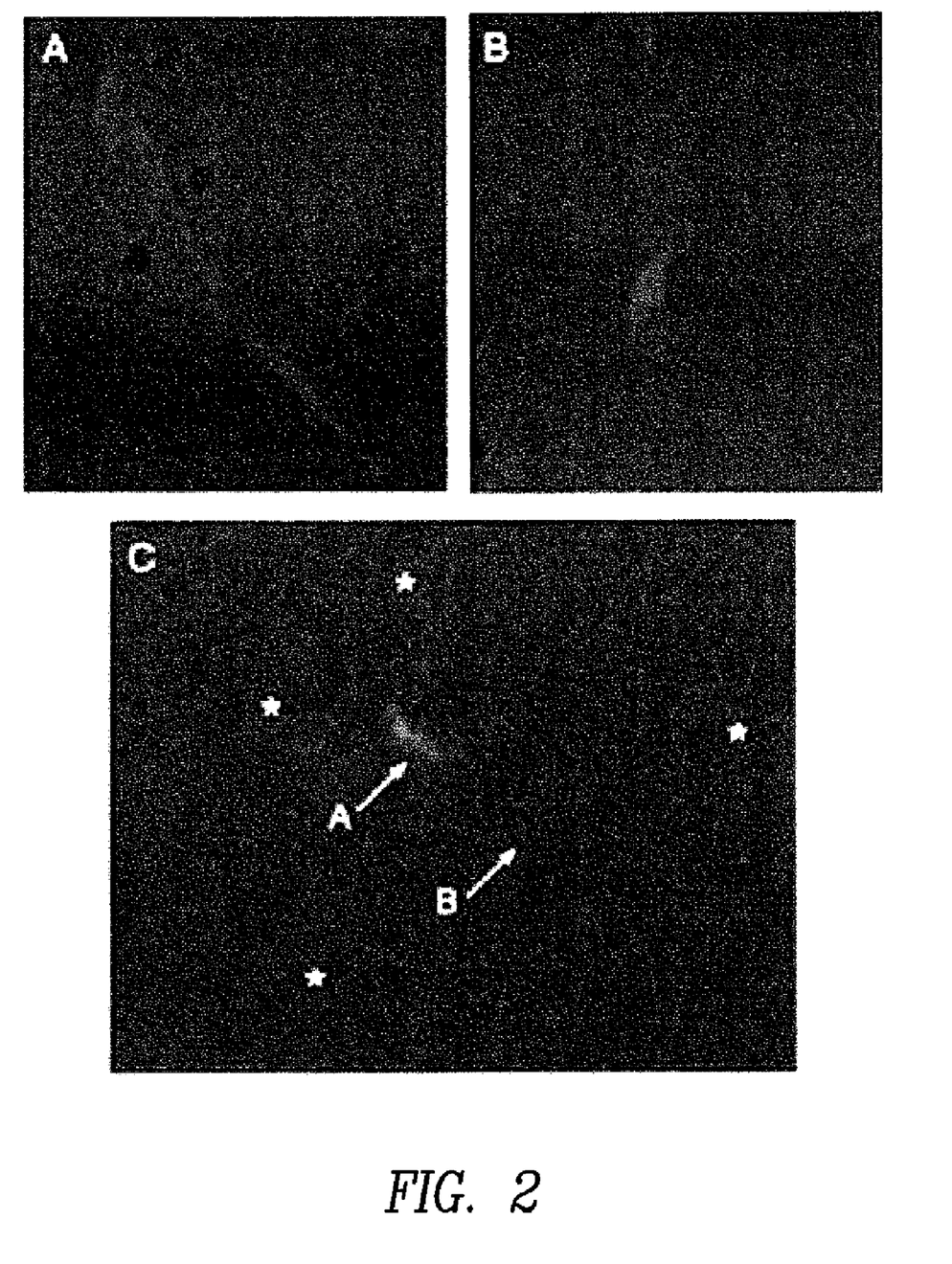
FIG. 2A is a standard fluorescent microscopic image of knockout sperm showing the absence SPAM1 on a control sperm.
FIG. 2B is a standard fluorescent microscopic image of the localization of epididymal SPAM1 (stained green-yellow) on the head of a knock-out sperm after binding thereon in a pattern seen in wild-type sperm from the caput region of the epididymis.
FIG. 2C is a standard fluorescent microscopic image of the localization of epididymal SPAM1 on head and tail of a knock-out sperm after binding thereon in a pattern seen in wild-type sperm from the caudal region of the epididymis.

The sperm were then washed to remove the mixture of tissue, luminal fluid and medium. To detect binding of Spam 1 on the sperm, sperm were fixed in 1.5% paraformaldehyde and then subjected to an immunocytochemistry procedure using Spam 1 anti-peptide as the primary antibody. This anti-peptide has been shown to be specific for Spam 1 antigen (Deng et al., 2000). The second antibody was conjugated with fluorescein isothiocyanate (FITC). Control sperm were incubated with the medium under identical conditions as those for the test sperm and processed similarly for antigen detection. Results can be seen in FIG. 2C where the sperm having Spam1 protein bound thereon were seen only in the dish with the test sample and demonstrated a yellow-green color on the acrosomal region of the head and the midpiece of the tail, such as would be seen in wild-type mice. The yellow-green staining of the SPAM 1 protein was particulate in manner, indicating movement of the protein on the surface as also normally occurs with wild-type normal sperm. This distribution of Spam1 after uptake therefore mimics the in vivo situation where the tail plasma membrane shows the characteristic patchy appearance.

Example 2

In Vitro Uptake of Epididymal Spam1 from Wild-Type Mice by Spam1 K/O Mouse Sperm Procedure Sperm-free epididymal luminal fluid (LF) was obtained from wild-type ICR mice. The LF was prepared by centrifugation (3,500×g for 20 min) to pellet sperm and cellular fragments and was shown to be sperm-free after microscopic examination. We co-incubated Spam1 K/O epididymal sperm (from all epididymal regions combined) with sperm-free unfractionated dilute LF (protein concentration 1-1.5 mg/ml) combined from all three regions at room temperature (RT) for 1 or 2 hr. Binding was performed after washing sperm in phosphate buffered saline (PBS) and 1 mM PMSF (protease inhibitor). The control consisted of sperm that were incubated only in PBS and 0.1% (w/v) bovine serum albumin (BSA). During co-incubation the dish was gently shaken to prevent the cells from settling at the bottom.

Following co-incubation, sperm were washed to remove unbound protein and then processed (fixed in 4% paraformaldehyde in PBS or unfixed, washed with PBS, blocked, treated with primary Spam1 antipeptide antibody, washed with PBS, treated with a FITC-conjugated secondary antibody) for immunochemical detection of bound ES. One sample incubated with the LF was treated with the primary antibody after peptide inhibition. Slides were imaged with confocal or standard fluorescence microscopy.

Results and Interpretation

Figure 1:
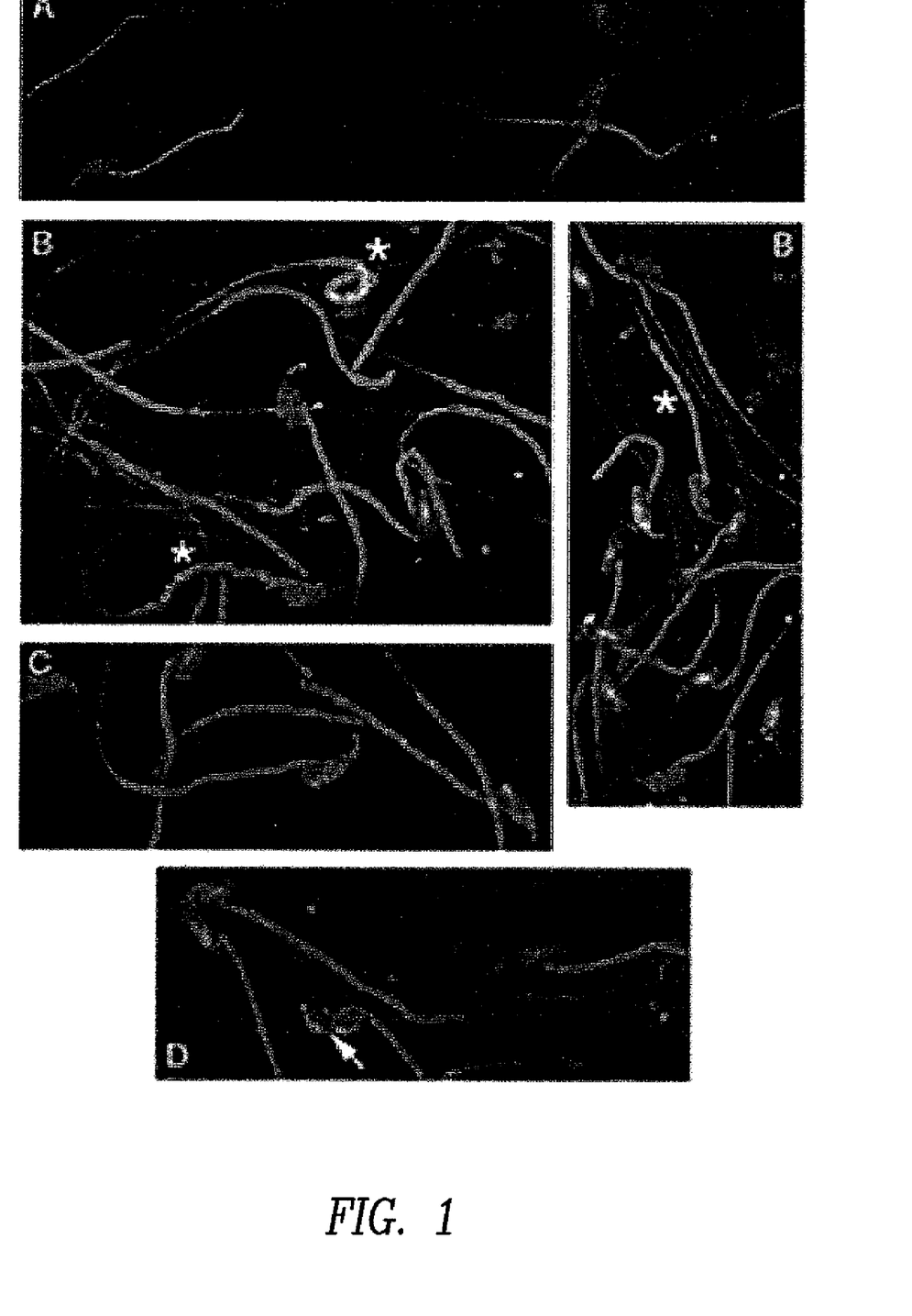
FIG. 1A is a confocal microscopic image showing only background fluorescence on the heads and tails of control knock-out sperm incubated only in PBS.
FIG. 1B is two panels showing of confocal microscopic images showing epididymal SPAM1 binding onto knock-out sperm in a pattern seen in wild-type sperm from the caput region of the epididymis; asterisks show binding on the tail.
FIG. 1C is a confocal microscopic image showing epididymal SPAM1 binding onto knock-out sperm in a pattern seen in wild-type sperm from in the corpus region of the epididymis.
FIG. 1D is two panels showing standard fluorescent images showing epididymal SPAM1 binding onto the head of knock-out sperm in a pattern seen wild-type sperm from the caudal region of the epididymis.

Our results provide proof of principle that sperm can bind ES in vitro. Since we pooled caput, corpus, and cauda epididymal sperm we observed different patterns of binding. ES was found uniformly distributed on the acrosomal region of the head and on the midpiece of the tail which are typical patterns seen in caput sperm (FIGS. 1-B, 2-B) and on the anterior head (in a crescent-shape) and the midpiece which are patterns seen in corpus and cauda wild-type sperm (FIGS. 1-C and D, 2-C). The staining is particulate or patchy, indicating movement of ES on the plasma membrane, as occurs in wild-type sperm. These distributions of ES mimic the patterns for wild-type sperm. Our results clearly show that sperm at different levels of maturity, by virtue of their different locations in the epididymis and the different binding patterns displayed, are capable of binding Spam1 in vitro. The sample with the antibody blockage by peptide inhibition showed markedly reduced staining, indicating antibody specificity.

Figure 3A:
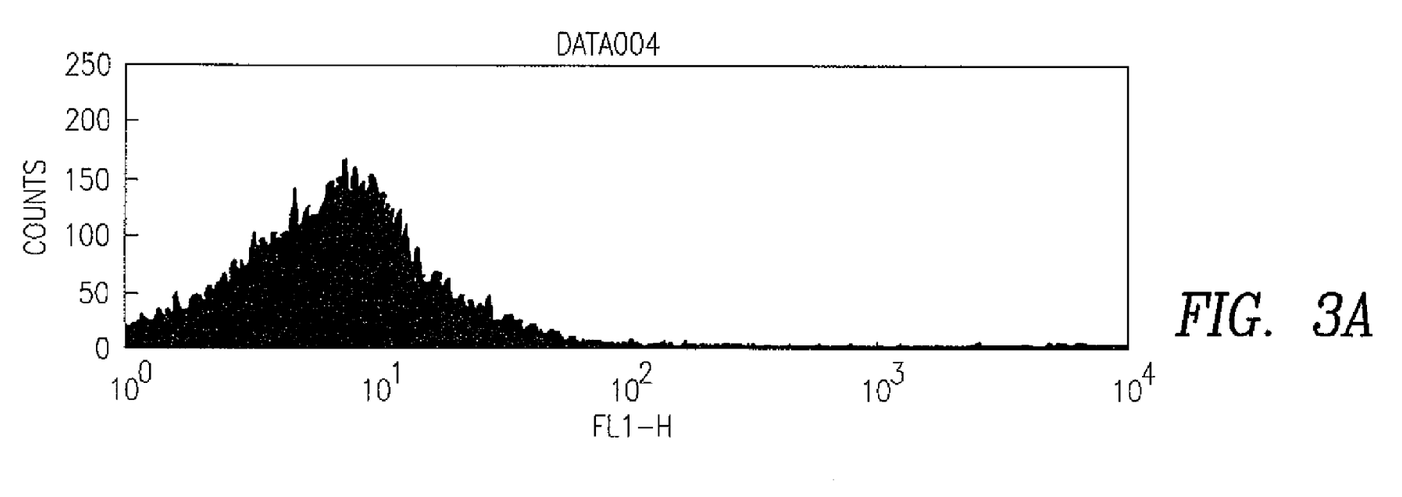
FIG. 3A is a flow cytometric analysis of a large population of control knockout sperm after incubation only in saline and detection of background fluorescence after staining with SPAM1 anti-peptide and a fluorescent secondary antibody.
Figure 3B:
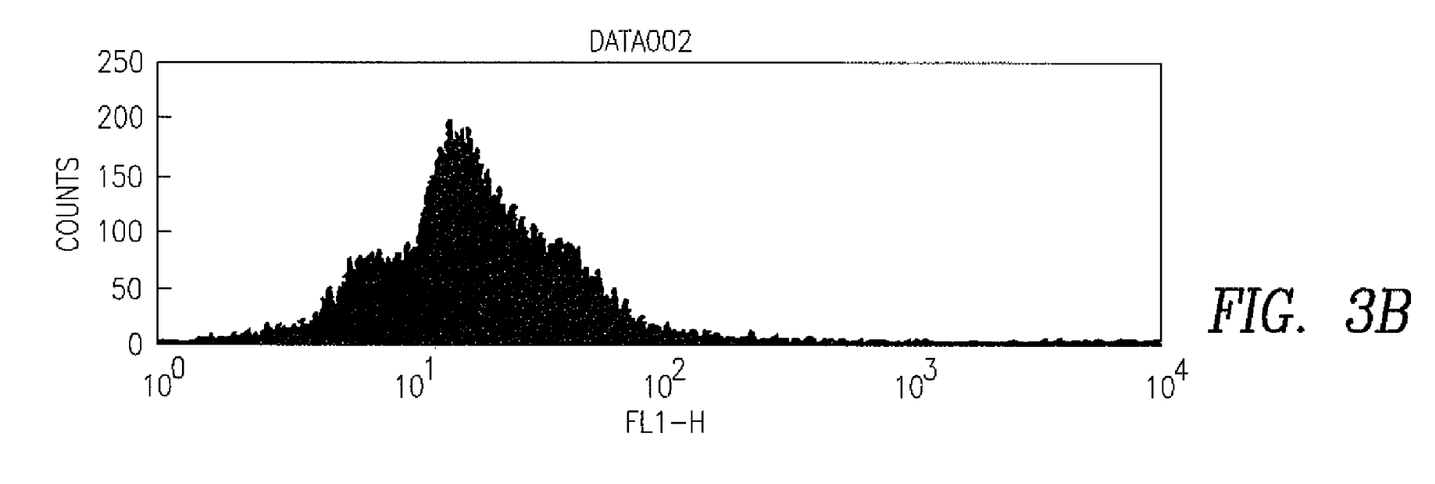
FIG. 3B is a flow cytometric analysis of a large population of knock-out sperm after epididymal SPAM1 binding (1.5 mg/ml) and staining with SPAM1 anti-peptide followed by detection with a fluorescent staining showing increased fluorescence.
Figure 3C:
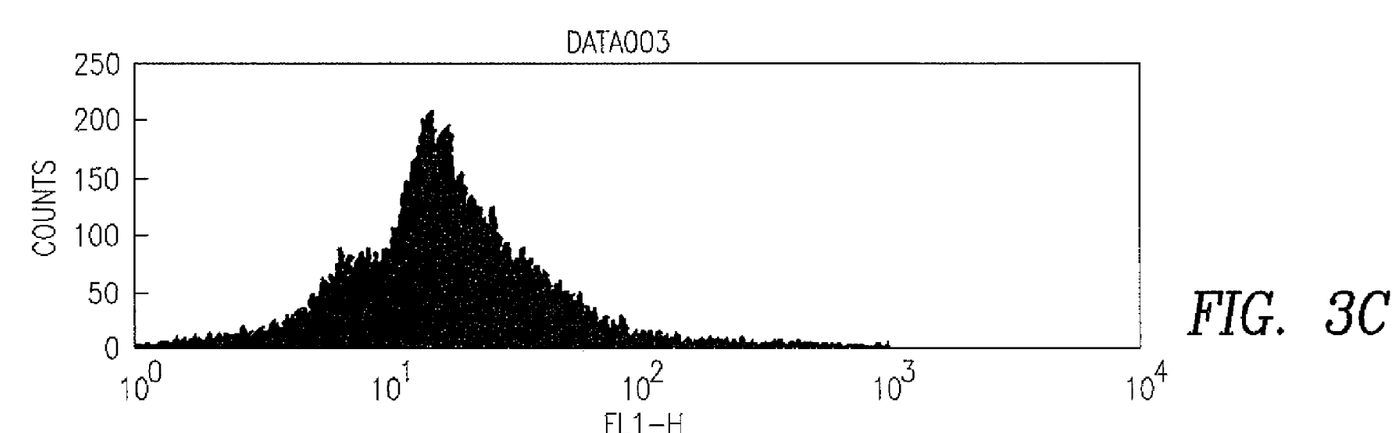
FIG. 3C is a flow cytometric analysis of a large population of knock-out sperm after epididymal SPAM1 binding (1 mg/ml) and staining with SPAM1 anti-peptide followed by detection with a fluorescent staining showing increased fluorescence.

To confirm and quantify the binding detected using immunofluorescence, flow cytometry was performed on 30,000 sperm from the test and control. The test groups showed higher fluorescence (FIGS. 3B and 3C) (right shift of the peak on the horizontal axis) and two sperm populations. The heterogeneity of the test populations, not seen in the control (FIG. 3A), suggests that there are subsets of sperm with and without ES. These results provide direct evidence that ES can be acquired by sperm from dilute epididymal LF.

Example 3

Figure 4:
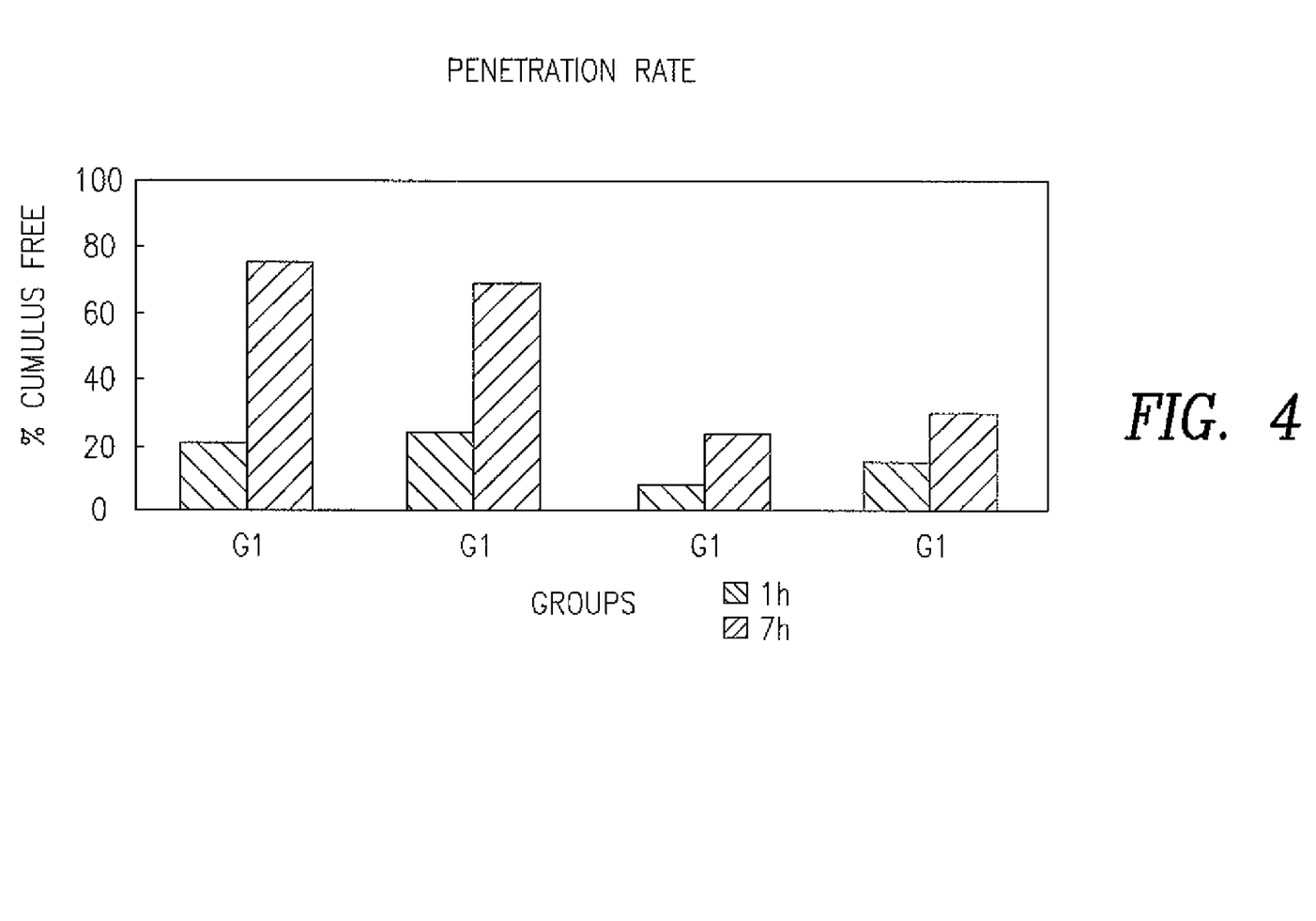
FIG. 4 is a bar graph showing the dispersal of cumulus cells from the cumulus mass in oocytes incubated for 1 hr and 7 hr with wild-type or knock-out sperm exposed in vitro during capacitation to SPAM1-containing luminal fluid from wild type of knock-out mice.

Spam1 K/O Sperm Penetrate Significantly More Cumulus-Intact Eggs After In Vitro Exposure to Wild-Type (WT) LF Untreated with Spam1 Antibodies To determine the impact of in vitro binding of epididymal Spam1 on fertilizing ability, sperm from wild-type or K/O mice were incubated with epididymal luminal fluid at 37° C. during a 45 min capacitation period at 37° C. in 5% $CO_2$, 5% $O_2$, and 90% $N_2$. Wild-type sperm were used as a positive control. K/O sperm were tested for their performance after exposure to K/O luminal fluid, wild-type luminal fluid and wild-type luminal fluid with Spam1 antibody inhibition. Thus wild-type luminal fluid was pre-incubated with the anti-Spam1 antibodies to block the Spam1 present or with pre-immune serum before sperm were added (this antipeptide antibody has been shown to be specific for Spam1 in a number of studies, including assays using peptide inhibition). The wild-type sperm used as a positive control were incubated with wild-type luminal fluid. After exposure to luminal fluid under capacitation conditions, aliquots of sperm were removed and used to inseminate freshly released cumulus-intact oocytes (eggs) from superovulated ICR females in in vitro fertilization assays. Eggs were monitored during incubation after the first hr and at 2 hour intervals thereafter up to 7 hours, to detect the progress of cumulus cell-removal which was categorized as stages 1-4, with stage 4 demonstrating complete dispersal of the cumulus cells. FIG. 4, which shows the penetration rate after 7 hours, demonstrates that the percentage of fertilization for K/O sperm incubated in antibody-inhibited luminal fluid was 23% (G3) compared to 69% in the absence of antibody inhibition of Spam1 for populations of 121 and 102 eggs, respectively. This reflects a significant difference in the behavior of these sperm under the specified conditions. It is noted that the rate of K/O sperm incubated in K/O luminal fluid is not significantly different from that for sperm from the antibody-inhibited luminal fluid (G3).

To determine that sperm bind Spam1 when exposed to luminal fluid under capacitation conditions, aliquots of K/O sperm used for insemination were subjected to immunocytochemistry for the detection of Spam1 on the sperm surface. Binding was shown to be present. Note also that although these experiments were performed with K/O sperm there is evidence to suggest that mature wild-type sperm are not at saturation levels with respect to Spam1 and can bind Spam1 in vitro. We have shown that mature caudal sperm can bind Spam1 secreted in the uterine fluid, suggesting that after wild-type sperm leave the male they are not at saturation levels for this protein.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A method for attaching at least one Sperm Adhesion Molecule 1 protein to one or more mature caudal sperm in an in vitro environment prior to implantation into a uterus, the method comprising combining said one or more mature caudal sperm to said at least one Sperm Adhesion Molecule 1 in an in vitro environment under capacitation conditions, prior to implantation into the uterus, wherein the Sperm Adhesion Molecule 1 comprises a lipid anchor, and whereby said at least one Sperm Adhesion Molecule 1 protein is attached to said one or more mature caudal sperm.

2. The method of claim 1 wherein the Sperm Adhesion Molecule 1 is obtained from the epididymis of a mammal.

3. The method of claim 1 wherein the sperm is exposed to epididymal luminal fluid comprising said at least one Sperm Adhesion Molecule 1.

4. The method of claim 3 wherein the epididymal luminal fluid comprises a sperm-free epididymal luminal fluid.

5. The method of claim 1 wherein the Sperm Adhesion Molecule 1 is obtained from the uterus of a mammal.

6. The method of claim 1 wherein the sperm is exposed to uterine luminal fluid comprising said at least one Sperm Adhesion Molecule 1.

7. The method of claim 6 wherein the uterine luminal fluid is sperm free.

8. The method of claim 1 wherein the Sperm Adhesion Molecule 1 is chemically bound to the membrane of the sperm via the lipid anchor.

9. The method of claim 1 wherein the one or more sperm is exposed to said at least one Sperm Adhesion Molecule 1 for a period of time ranging from about 5 to about 120 minutes.

10. The method of claim 3 wherein the concentration of Sperm Adhersion Molecule 1 protein in the epididymal luminal fluid is about 0.1 to 2.0 mg/ml.

11. The method of claim 6 wherein the concentration of Sperm Adhesion Molecule 1 in the unterine luminal fluid is about 0.1 to 2.0 mg/ml.

12. The method of claim 1, wherein the in vitro environment is supplemented with SPAM1.

* * * * *